(12) United States Patent
Ohlemeyer et al.

(10) Patent No.: US 6,421,990 B1
(45) Date of Patent: Jul. 23, 2002

(54) MEASURING DEVICE FOR MEASURING COMPONENTS IN AND/OR PROPERTIES OF CROP MATERIAL

(75) Inventors: Heinrich Ohlemeyer, Ludwigshafen; Georg Kormann, Kirrberg, both of (DE)

(73) Assignee: Deere & Company, Moline, IL (US)

( * ) Notice: Subject to any disclaimer, the term of this patent is extended or adjusted under 35 U.S.C. 154(b) by 0 days.

(21) Appl. No.: 09/573,317

(22) Filed: May 18, 2000

(30) Foreign Application Priority Data

May 19, 1999 (DE) ......................... 199 22 867
Mar. 1, 2000 (EP) ............................. 00104194

(51) Int. Cl.⁷ ............................... A01D 75/28
(52) U.S. Cl. ................... 56/10.2 R; 356/328
(58) Field of Search ............... 356/402–411, 330–334, 356/326, 328, 346, 237; 250/226, 339.12, 339.02, 910; 56/10.2 R; 460/4, 6, 7

(56) References Cited

U.S. PATENT DOCUMENTS

| | | | |
|---|---|---|---|
| 3,805,497 A | 4/1974 | Ross | 56/10.4 |
| 4,830,194 A | 5/1989 | Kajiura et al. | 209/580 |
| 5,258,825 A | * 11/1993 | Reed et al. | 356/402 |
| 5,327,708 A | 7/1994 | Gerrish | |
| 5,406,084 A | * 4/1995 | Tober et al. | 250/339.01 |
| 5,751,421 A | 5/1998 | Wright et al. | 356/328 |
| 5,991,025 A | * 11/1999 | Wright et al. | 356/328 |
| 6,100,526 A | * 8/2000 | Mayes | 250/339.11 |
| 6,115,115 A | * 9/2000 | Skarie et al. | 356/73 |

FOREIGN PATENT DOCUMENTS

| | | |
|---|---|---|
| DE | 32 11 731 A1 | 10/1983 |
| DE | 32 32 746 C2 | 8/1984 |
| EP | 0 615 682 A1 | 9/1994 |
| EP | 0 511 184 A1 | 10/1999 |
| GB | 1270535 | 4/1972 |
| WO | WO 99 40419 | 8/1999 |

\* cited by examiner

*Primary Examiner*—Robert E. Pezzuto
*Assistant Examiner*—Árpád Fab Kovács

(57) ABSTRACT

A self-propelled crop harvester or one of the train of towing vehicle and towed implement for processing harvested crop are equipped with a measuring device for the measurement of components in and/or properties of harvested crop that is conveyed along a path and/or along which the measuring device is moved. The measuring device is an optical spectroscope which operates in the visible wavelength range and/or in the near infrared wavelength range. Measurements made are used to determine the amount of particular organic components contained in the harvested crop, such as carbohydrates, organic substances that can be dissolved in enzymes, oil and raw protein; and to determine the amount of non-organic components contained in the harvested crop, such as minerals, for example sodium and magnesium or water. Further parameters of the harvested crop are also measured including solid matter and raw fiber content, length of fibers, caloric or energy content, digestibility and color.

7 Claims, 5 Drawing Sheets

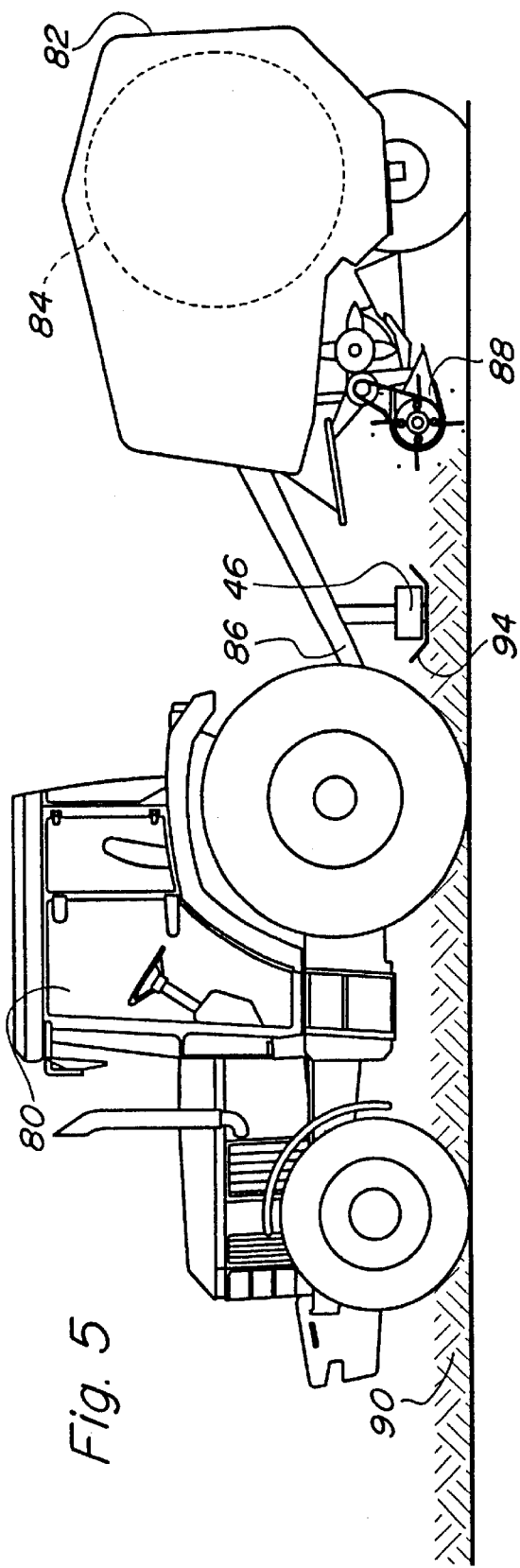
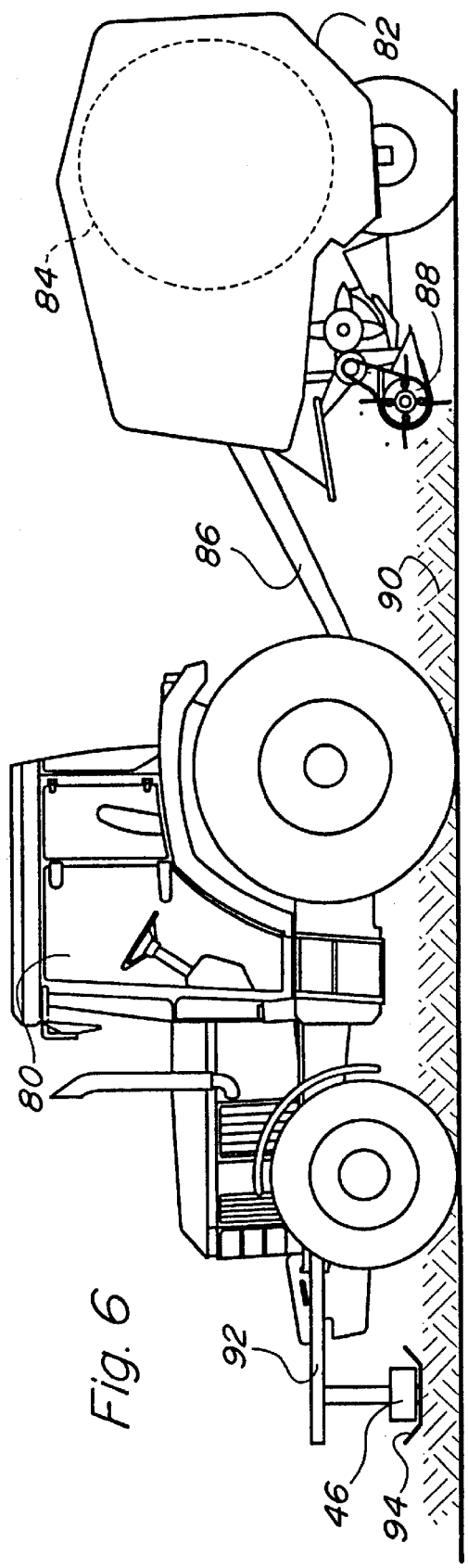

MEASURING DEVICE FOR MEASURING COMPONENTS IN AND/OR PROPERTIES OF CROP MATERIAL

The present invention pertains to a measuring device for measuring components in and/or properties of crop material that is conveyed along a path and/or past the measuring device.

BACKGROUND OF THE INVENTION

In the state of the art (DE 196 48 126 A), harvesting machines that are equipped with devices for measuring the crop throughput, moisture and mass or density are known. The surface moisture of the crop material is measured by an infrared sensor while the layer thickness and density, as well as the moisture of the crop, is measured by microwaves with wavelengths from 1m down to less than approximately 0.5 mm.

DE 32 32 746 C describes a harvesting machine, in particular a baler, a self-loading forage box or a combine equipped with a moisture sensor that is provided along the path traveled by the harvested crop as it passes through the machine.

However, not all parameters needed for the additional usage of the crop material are obtained by these measurements. Of interest for further processing would be, for instance, the protein and/or fat content, digestibility, caloric value, fiber length and content, and so on.

U.S. Pat. No. 5,327,708 proposes a system for the investigation of harvested crop. On a combine, a sample is taken at regular time intervals from the flow of the crop reaching the grain tank and is examined by means of an appropriate arrangement for its mass, moisture content and density. Other parameters of the crop such as protein, sugar and oil contents, and color can also be measured. The system limits the detection of values to discrete locations so that a yield ticket would contain a number of gaps.

The problem underlying the invention is seen in the fact that a yield ticket specific to a partial area of the parameters with the measurement system disclosed in U.S. Pat. No. 5,327,708 contains gaps. A laboratory analysis to produce a yield ticket is very costly due to the large number of samples required to be taken and analyzed in order to leave no gaps.

SUMMARY OF THE INVENTION

According to the present invention, a harvesting arrangement is equipped with a measuring system which overcomes the drawbacks of the prior art systems.

An object of the invention is to provide a harvesting arrangement equipped with a measuring system which continuously samples crop as the crop travels through the arrangement, or as the arrangement passes over the crop, so as to obtain data from which organic and/or non-organic crop components may be determined.

A further object of the invention is to provide a crop harvesting arrangement equipped with a measuring system, that is used in lieu of or in addition to the measuring system defined in the preceding object, which continuously samples crop as it travels through the arrangement, or as the arrangement passes over the crop, so as to obtain data from which the content of solid matter such as raw fiber content, length of fiber, digestibility, the energy content of the harvested crop may be continuously obtained.

Yet another object of the invention is to provide a harvesting arrangement equipped with a measuring device, as set forth in the previous objects, wherein the harvesting arrangement is also equipped with a geographical locating system so that the data can be correlated to specific areas of the field from which the crop was harvested.

These and other objects will become apparent from a reading of the ensuing description together with the appended drawings.

BRIEF DESCRIPTION OF THE DRAWINGS

FIG. 5 is a schematic representation of a train of a tractor towing a baler equipped with a crop component content sensor.

FIG. 6 is a view like FIG. 5 but showing the tractor equipped with the crop component content sensor.

DESCRIPTION OF THE PREFERRED EMBODIMENT

Figure 1:
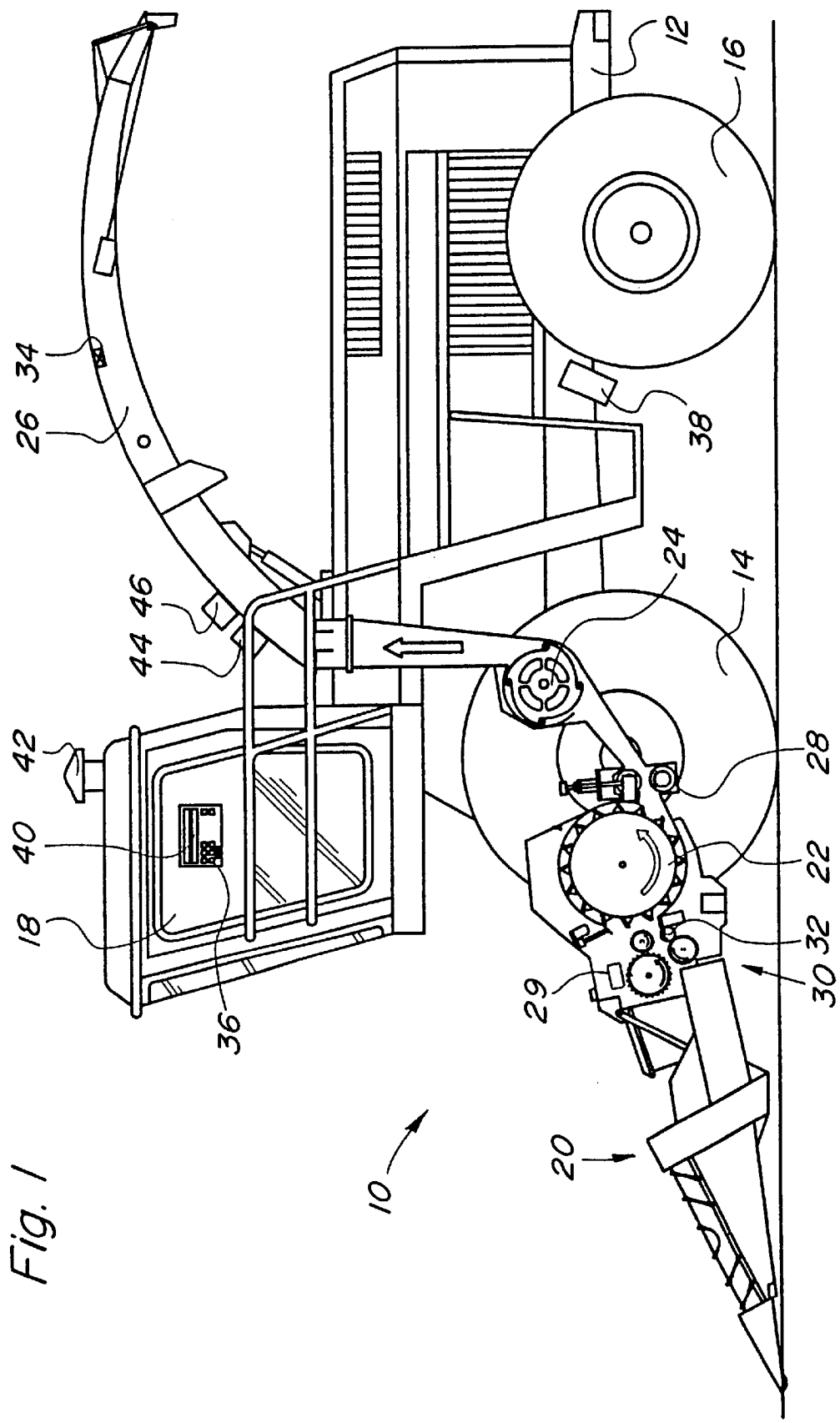
FIG. 1 is a schematic left side view of a harvesting machine embodying the present invention.

Referring now to FIG. 1, there is shown a harvesting arrangement in the form of a crop harvesting machine 10 here illustrated as a self-propelled forage harvester including a chassis 12 supported by front and rear sets of wheels 14 and 16, respectively. The operation of the harvesting machine 10 is controlled from a driver's cabin 18 from which a crop material intake device, that is coupled to the front of the chassis 12, can be easily seen. By means of the crop material intake device 20, which is a row-independent corn cutter in this embodiment, material picked up from the ground such as corn, grass or the like, is fed to a chopping drum 22, which chops it into small pieces and transfers it to a conveyor arrangement 24. The crop leaves the harvesting machine 10 to an accompanying trailer (not shown) through a discharge duct or spout 26, which is mounted for swiveling about an upright axis. Between the chopping drum 22 and the conveyor device 24, there extends a kernel processor 28 through which the conveyed material is tangentially fed to the conveyor device 24. Additional details of the harvesting machine 10 require no description as it is conventionally known.

On the harvesting machine 10 shown in FIG. 1, several sensors are provided for the measurement of the flow of crop material passing through the harvesting machine 10 per unit time, the so-called throughput. A first throughput sensor 29 measures the spacing between two pre-compression rolls 30, that are arranged between crop material intake unit 20 and the chopping drum 22, and between which the harvested crop is conveyed. The sensor 29 is in the form of a sliding or rotary resistor (potentiometer) that is coupled for being actuated by the upper roll 30, which is commonly resiliently suspended for rising and falling motion in response to variations in the thickness and density of the conveyed crop passing between the rolls 30. Additionally, the rotational speed of one of the pre-compression rolls 30 is measured by means of a second sensor 32. Beyond that, additional sensors may measure the propulsion torque of the conveyor arrangement 24 and the regrinding arrangement 28.

An on-board computer 40 connected to a display 36 serves to record and evaluate the measured data.

A sensor in the form of a light barrier 34 is arranged in the discharge duct 26 to determine whether any harvested crop material is being conveyed through the harvesting machine 10. Acquisition of measured data takes place only if the light barrier 34 detects a conveyance of crop material. The volume of crop flow, that is the rate at which crop flows through the harvesting machine 10 per unit time, can be calculated by the spacing of the pre-compression rolls 30 and their rotations per minute or rotational speed. Due to the compression by the pre-compression rolls 30, an approximately constant density of the harvested crop is achieved. Under this presupposition, the volume flow is directly proportional to the mass flow. The light barrier 34 provides information as to whether crop material is present in the discharge duct 26. All the measurement signals can be triggered with this information. A measurement thus takes place only if the light barrier 34 detects material. The light barrier 34 additionally allows a correction function because, in case of very low crop material flow, it is possible that the movably mounted pre-compression roll 30 might not have undergone an upward excursion, but crop material is nonetheless present. This state of affairs is recognized from the signal of the light barrier 34, and the crop material flow can be corrected utilizing a constant corrective factor or summation.

In addition, in order to calculate a yield, information on the actual vehicle speed and working width are also needed. The vehicle speed can be obtained from data of the propulsion units of the harvesting machine 10 or acquired by a radar sensor 38. By means of a global positioning system (GPS) sensor 42, the yield of a specific area in the field can be ticketed or plotted by the on-board computer 40.

The harvesting machine 10 is additionally equipped with a moisture measuring device 44 for measuring the moisture of the crop material. This can be accomplished in a conventional manner, for instance, by conductivity measurement, dielectrically or capacitatively, with microwaves, or optically in the near infrared range. These measuring processes are conventionally known and require no further explanation.

According to the invention, a measuring device 46 is provided for the measurement of the contents of certain components of the harvested crop. The measurement processes of the measuring device 46 is preferably optical spectroscopy in the visible wavelength region and/or in the near infrared region. The wavelengths employed lie between 100 nm and 1 mm, preferably between 400 nm and 1.7 µm. In this wave length range, the organic components, in particular, can be detected particularly well. As a rule, here a calibration of the optically operating measuring device 46 will be appropriate. The signal from the light barrier 34 is used for triggering or activating the measuring device 46. Thereby, water, raw protein, fat, and other contents of the crop material can be displayed on and stored in a geographically referenced form in the on-board computer 40. The measuring device 46 is also set up to detect additional parameters of the crop material, namely fiber length, fiber content and content of solid dry matter.

Figure 2:
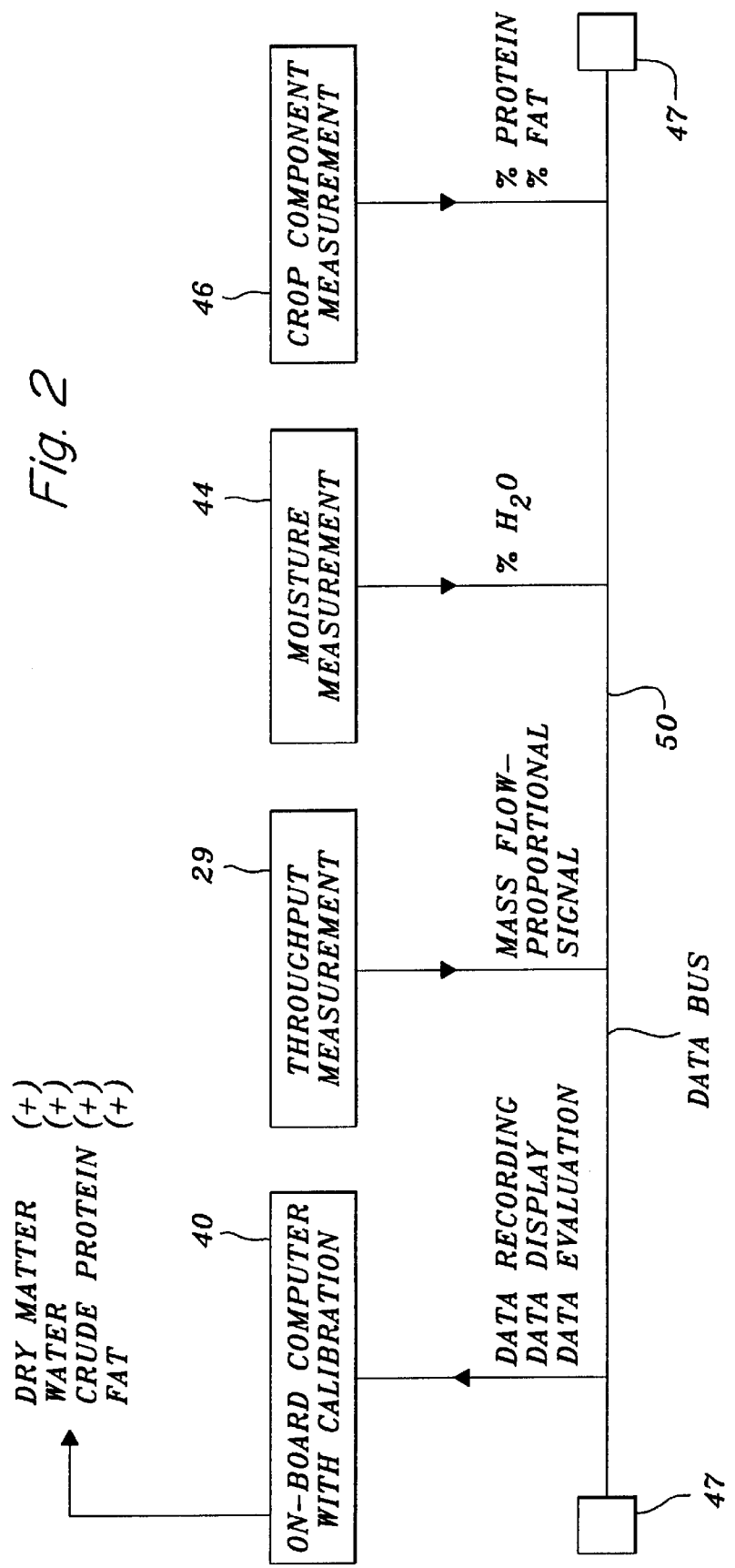
FIG. 2 is a circuit diagram of the on-board computer and various sensors for collecting crop-specific data to be processed by the computer.

Reproduced in FIG. 2 is a schematic circuit diagram that shows the connection, by way of a data bus 50, between the on-board computer 40 and the throughput sensor 29, the moisture-measuring device 44 for measurement of the moisture content of the harvested crop, and the crop component content measuring device 46. The data bus 50 obviates the need to lay separate cables, and can also be connected to additional devices of the harvesting machine 10 such as the engine and the operating units as indicated by the small rectangles 47 at either end of the bus 50. If the data bus 50 is used only for the measuring device, it must be blocked at both ends by blocking resistors. The drawing schematically illustrates that the on-board computer 40 is supplied with a signal from the throughput sensor 34 that is proportional to the mass flow, a signal from the moisture measuring device 44 that contains information about the water content of the harvested crop, and a signal from the measuring device 46 that provides the content of certain components of the harvested crop, such as protein or fat. This information is continuously displayed and stored in memory.

Figure 3:
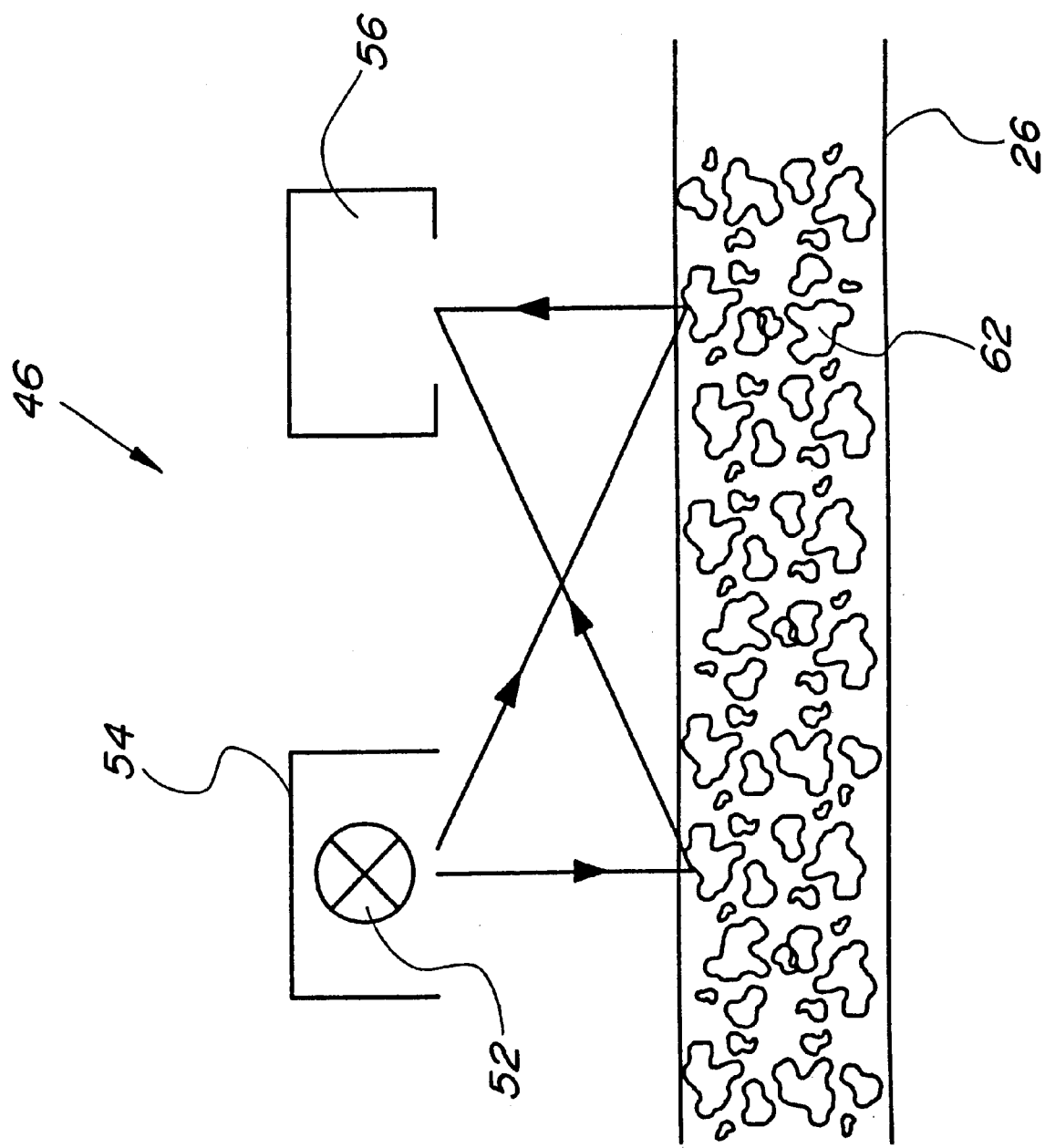
FIG. 3 is a schematic representation of a device for measuring the content of crop components.

A measuring device 46 is presented in FIG. 3. It comprises a lamp 52 which is arranged inside a lamp housing 54, and whose broad band (white) light reaches the interior of the discharge duct 26 through which the harvested crop 62 flows. Light reflected by the harvested crop 62 flowing through the duct 26 reaches a sensor 56, whose detailed structure can be seen in FIG. 4.

Figure 4:
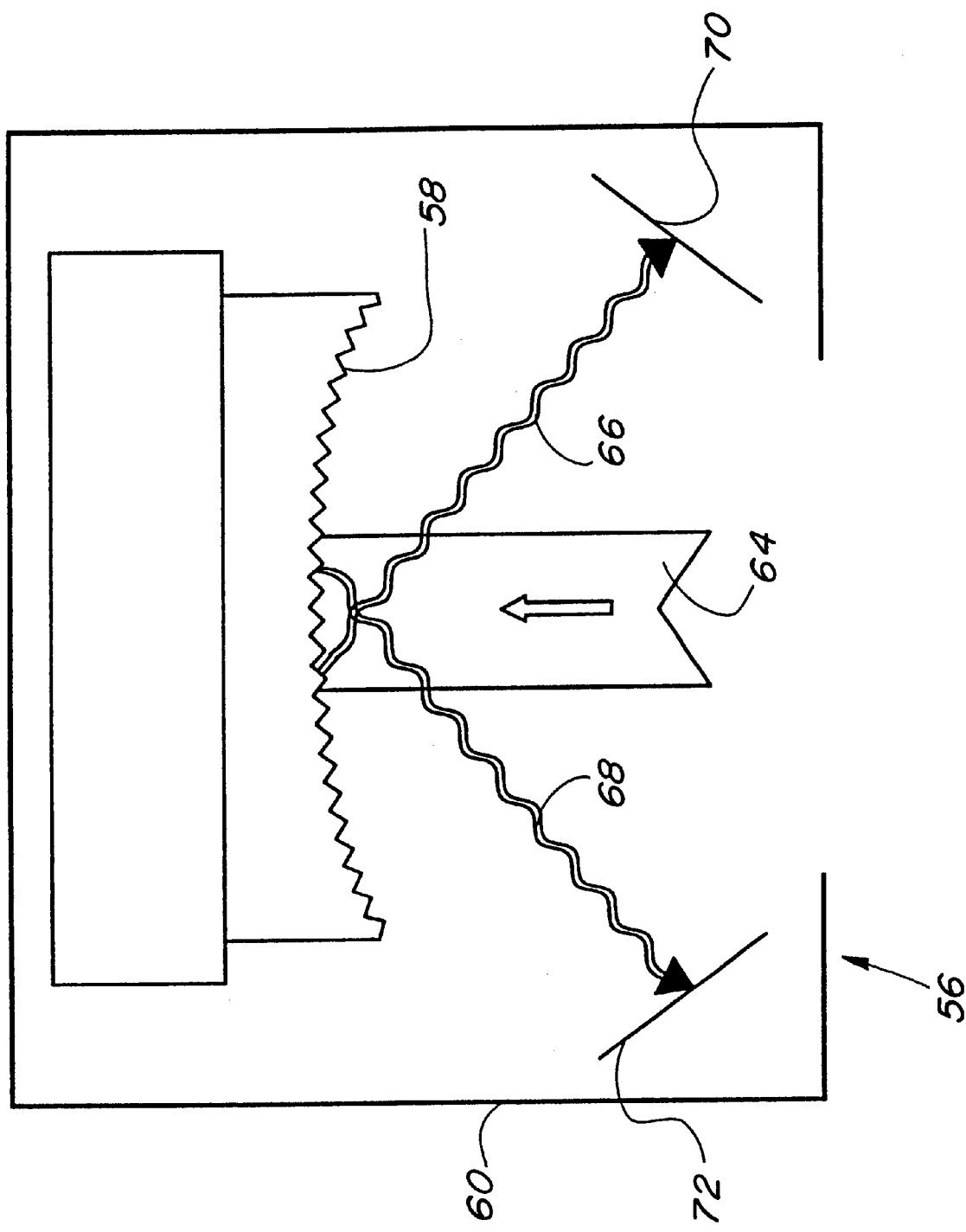
FIG. 4 is a schematic representation of the crop component content sensor of the device shown in FIG. 3.

The sensor 56 has a housing 60, in the interior of which is arranged a parabolic mirror 58 featuring a surface having projections of triangular cross section. The projections extend perpendicular to the plane of the drawing. The parabolic mirror 58 scatters the broad band light 64 reflected from the harvested crop 62 in directions dependent on wave length by means of constructive or destructive interference, since the projections are dimensioned relatively small, although represented in exaggeratedly large dimensions in the drawing. The result is two light beams or rays 66 and 68, respectively comprising a different wavelength range, are reflected from the mirror 58 so as to be deflected to the left and to the right, as seen in FIG. 4. The light beams 66 and 68 reach their respective detectors 70 and 72. The detectors 70 and 72 include several light sensitive elements, such as semiconductor detectors, in particular, CCDs, or photo diodes of silicon (Si) or indium-gallium-arsenide (InGaAS) arranged one alongside the other. Therefore, the output signal of each element of the detectors 70 and 72 corresponds to the received intensity in a given light wavelength range, which is defined by the position of the element of detectors 70 and 72 and the diffraction direction of the mirror 58. Based on the output signals of the elements of the detectors 70 and 72, an evaluation of the spectra measured can be performed by a computer assigned to the measuring device 46 or with the on-board computer 40, on the basis of which the determination of the proportions of certain crop components is possible. Near infrared and visible light, e.g., the range from 400 nm to 1700 nm, can be considered as the wavelength range.

It would be conceivable, in place of the mirror 58 equipped with the grating, to use only wavelength dependent scattering of the light of a least one prism, that resolves the light spectrally by its dispersion.

It should be noted that any measuring device 46 that operates in the visible and/or the infrared wavelength range or region can be used. Hence, in place of the mirror 58 with a grid, as shown, or of prisms, there could be filters arranged to freely rotate on a disk, for example, as are disclosed in EP 511184 A and the references cited therein.

FIG. 5 shows a measuring device 46 arranged between a tractor 80 and a baler 82 coupled to it. The baler 82 is provided with a crop intake arrangement 88 in the form of a pick-up and shapes crop that is taken up, in particular grass, into a bale 84. The measuring device 46 is arranged on the tow-bar 86 between the tractor 80 and the baler 82 on a skid 94, that slides over the harvested crop deposited in a swath or windrow 90. Thereby the measuring device 46 is arranged immediately above the swath 90 of harvested crop and can detect its characteristics without any problem.

In FIG. 6, the measuring device 46 is fastened to a suspension 92 secured to and projecting forwardly from the font of the tractor 80. In a manner similar to that described above, the measuring device 46 is carried by the skid 94 which is positioned for sliding over the harvested crop deposited in the swath or windrow 90.

What is claimed is:

1. In a combination of an agricultural apparatus for gathering windrowed crop and conveying the gathered crop along a confined path, and a measuring device for measuring crop components or properties, the improvement comprising: said measuring device being mounted on said agricultural apparatus in proximity to said windrow for continuously taking measurements as said agricultural apparatus advances along said windrow; and said measuring device being an optical spectrograph mounted for permitting light generated by said spectrograph to be reflected off said windrow with the reflected light being processed for determining at least one item in each of the following:

a. content of each of one or more organic substances contained in the crop, b. content of each of one or more non-organic substances contained in the crop, and/or c. qualities of the crop including one or more of digestibility, energy content, raw fiber content, fiber length or color.

2. The combination defined in claim 1 wherein said agricultural apparatus is an implement towed by a tractor and said measuring device is mounted on one of said implement and tractor in a position for traveling over said wind row during operation of said implement.

3. The combination defined in claim 2 wherein said implement has a tow bar coupled to said tractor; and said measuring device being mounted to said tow bar.

4. The combination defined in claim 3 wherein a skid is mounted to said tow bar for traveling over said windrow; and said measuring device being mounted to said skid.

5. The combination defined in claim 2 wherein said measuring device is mounted on said tractor in a position for traveling over said windrow during baling operation.

6. The combination defined in claim 5 wherein said measuring device is mounted to a forward end of said tractor.

7. The combination defined in claim 6 wherein a skid is mounted to said forward end of said tractor; and said measuring device being mounted to said skid.

\* \* \* \* \*